US008755878B2

(12) United States Patent
Tomimori et al.

(10) Patent No.: US 8,755,878 B2
(45) Date of Patent: Jun. 17, 2014

(54) HEARTBEAT SIGNAL PROCESSOR AND HEARTBEAT SIGNAL PROCESSING METHOD

(71) Applicant: Fujitsu Limited, Kawasaki (JP)

(72) Inventors: Hideki Tomimori, Kawasaki (JP); Satoshi Sano, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/710,566

(22) Filed: Dec. 11, 2012

(65) Prior Publication Data

US 2013/0150743 A1 Jun. 13, 2013

(30) Foreign Application Priority Data

Dec. 13, 2011 (JP) .................................. 2011-272004

(51) Int. Cl.
*A61B 5/0404* (2006.01)

(52) U.S. Cl.
USPC .......................................................... 600/521

(58) Field of Classification Search
USPC .......................................................... 600/521
See application file for complete search history.

(56) References Cited

U.S. PATENT DOCUMENTS

| 4,248,244 | A | 2/1981 | Charnitski et al. |
| 5,365,934 | A | 11/1994 | Leon et al. |
| 6,018,677 | A | 1/2000 | Vidrine et al. |

| 2008/0200823 | A1 | 8/2008 | Cho et al. |
| 2011/0125002 | A1 | 5/2011 | Ershov et al. |
| 2012/0116239 | A1 | 5/2012 | Kato |

FOREIGN PATENT DOCUMENTS

| JP | 2009-142576 | 7/2009 |
| WO | WO 2011/018855 A1 | 2/2011 |

OTHER PUBLICATIONS

Extended European Search Report issued Apr. 15, 2013 in corresponding European Application No. 12195902.7.

*Primary Examiner* — Michael Kahelin
(74) *Attorney, Agent, or Firm* — Staas & Halsey LLP

(57) ABSTRACT

A heartbeat signal processor includes a first and second electrodes to obtain a first and second heartbeat signals, a DC voltage calculating unit and an AC amplitude calculating unit to calculate first and second average DC voltage values of direct-current components and first and second average AC amplitude values of alternate-current components in the first and second heartbeat signals, a correlation coefficient calculating unit to calculate a correlation coefficient between the alternate-current components in the first and second heartbeat signals, an amplification factor setting unit to set an amplification factor on the basis of the first and second average DC voltage values, the first and second average AC amplitude values, and the correlation coefficient, and a signal generating unit to generate a differential heartbeat signal by amplifying the first or second heartbeat signal on the basis of the amplification factor and calculating a difference between the first and second heartbeat signals.

7 Claims, 7 Drawing Sheets

US 8,755,878 B2

HEARTBEAT SIGNAL PROCESSOR AND HEARTBEAT SIGNAL PROCESSING METHOD

CROSS-REFERENCE TO RELATED APPLICATION

This application is based upon and claims the benefit of priority of the prior Japanese Patent Application No. 2011-272004, filed on Dec. 13, 2011, the entire contents of which are incorporated herein by reference.

FIELD

The embodiments discussed herein are related to a heartbeat signal processor and a heartbeat signal processing method.

BACKGROUND

To avoid drowsy operation by the operator of an automatic device or the like, it has been studied to measure the heartbeat of the operator and detect the drowsiness or arousal level of the operator on the basis of the measured heartbeat (e.g., Japanese Laid-open Patent Publication No. 2009-142576).

In a vehicle, for example, electrodes are provided in the steering wheel or any other location to be brought into contact with the driver. When the driver touches the electrodes, an electrocardiographic signal of the driver may be detected. The detected electrocardiographic signal is subjected to noise reduction processing or other signal processing. The heartbeat of the driver may be measured by, for example, analyzing the heartbeat signal called the R wave included in the electrocardiographic signal subjected to signal processing.

A heartbeat signal detected by electrodes includes a lot of noise signals. It is difficult to measure accurately the heartbeat of the driver unless the noise signals detected together with the heartbeat signal are appropriately processed.

SUMMARY

According to an aspect of the invention, a heartbeat signal processor includes a first electrode configured to be gripped with one hand to detect a first heartbeat signal, the first heartbeat signal being a potential difference signal with respect to a reference potential, a second electrode configured to be gripped with another hand to detect a second heartbeat signal, the second heartbeat signal being another potential difference signal with respect to the reference potential, a DC voltage calculating unit configured to calculate first and second average DC voltage values as voltage values of direct-current components in the first and second heartbeat signals, an AC amplitude calculating unit configured to calculate first and second average AC amplitude values as amplitude values of alternate-current components in the first and second heartbeat signals, a correlation coefficient calculating unit configured to calculate a correlation coefficient between the alternate-current component in the first heartbeat signal and the alternate-current component in the second heartbeat signal, an amplification factor setting unit configured to set an amplification factor for amplifying the first or second heartbeat signal on the basis of the first and second average DC voltage values, the first and second average AC amplitude values, and the correlation coefficient, and a signal generating unit configured to generate a differential heartbeat signal by amplifying the first or second heartbeat signal on the basis of the amplification factor set by the amplification factor setting unit and calculating a difference between the first and second heartbeat signals.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENTS

A heartbeat signal processor and a heartbeat signal processing method according to the embodiments will now be described in more detail with reference to the drawings. Examples in which the heartbeat signal processor and heartbeat signal processing method according to the embodiments are applied to a driver operating a vehicle are described below. The heartbeat signals of the driver are detected, for example, when the driver grips the electrodes installed in the steering wheel in the vehicle.

Figure 1A:
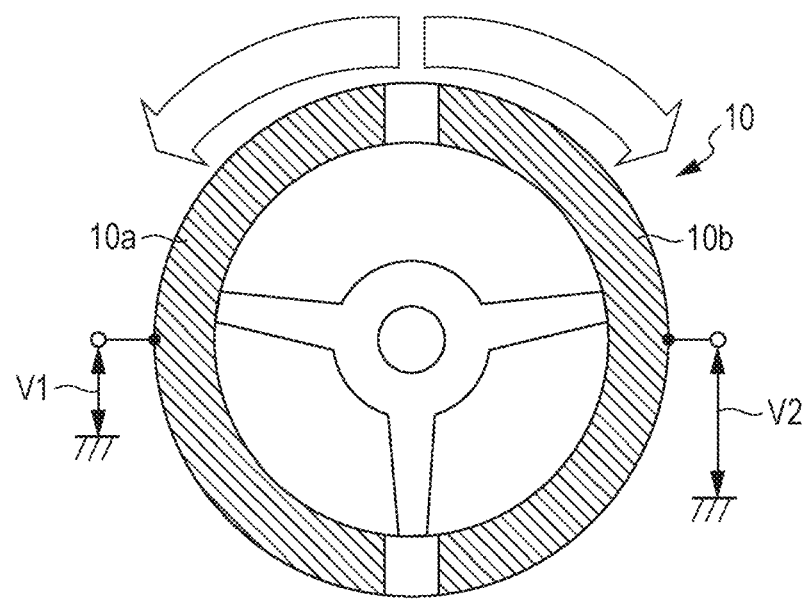
FIGS. 1A and 1B are diagrams illustrating exemplary locations of electrodes provided in a steering wheel of a vehicle.
Figure 1B:
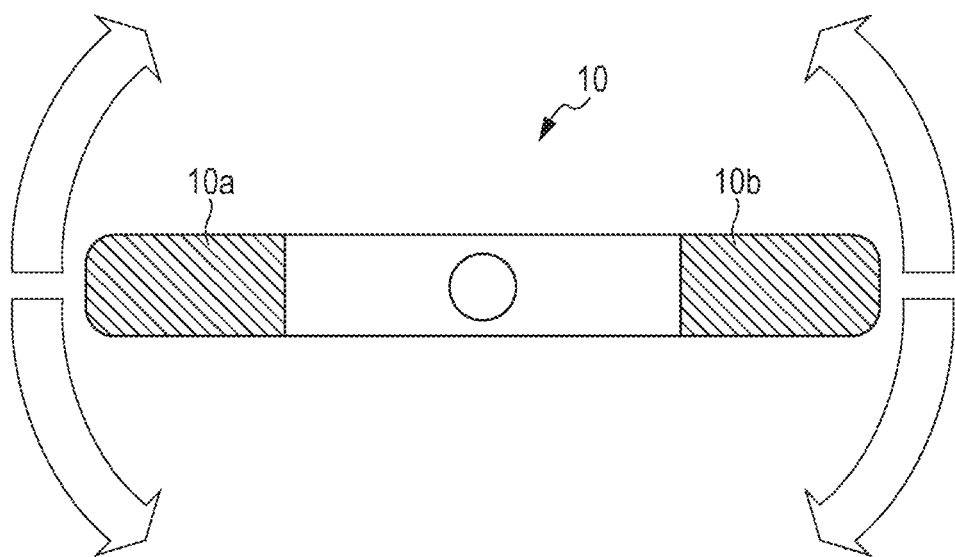

FIGS. 1A and 1B are diagrams illustrating exemplary locations of the electrodes provided in the steering wheel of a vehicle. The steering wheel 10 provided in a typical vehicle is formed in an annular shape as illustrated in FIG. 1A. A left-hand electrode 10$a$ and a right-hand electrode 10$b$ are provided in the steering wheel 10 at positions gripped by the left and right hands of the driver. In FIGS. 1A and 1B, the electrodes 10$a$, 10$b$ provided in the steering wheel 10 are indicated by hatching. The electrodes 10$a$, 10$b$ may be provided solidly all over the steering wheel 10 or in the form of a mesh. When the left and right hands of the driver touch the electrodes 10$a$, 10$b$, respectively, potential differences (voltages) V1 and V2 are produced in the electrodes 10$a$, 10$b$ with respect to a reference potential such as ground. Changes over time in potential differences V1 and V2 correspond to the heartbeat signals of the driver. The steering wheel may also have a lever-like shape as illustrated in FIG. 1B.

Figure 2A:
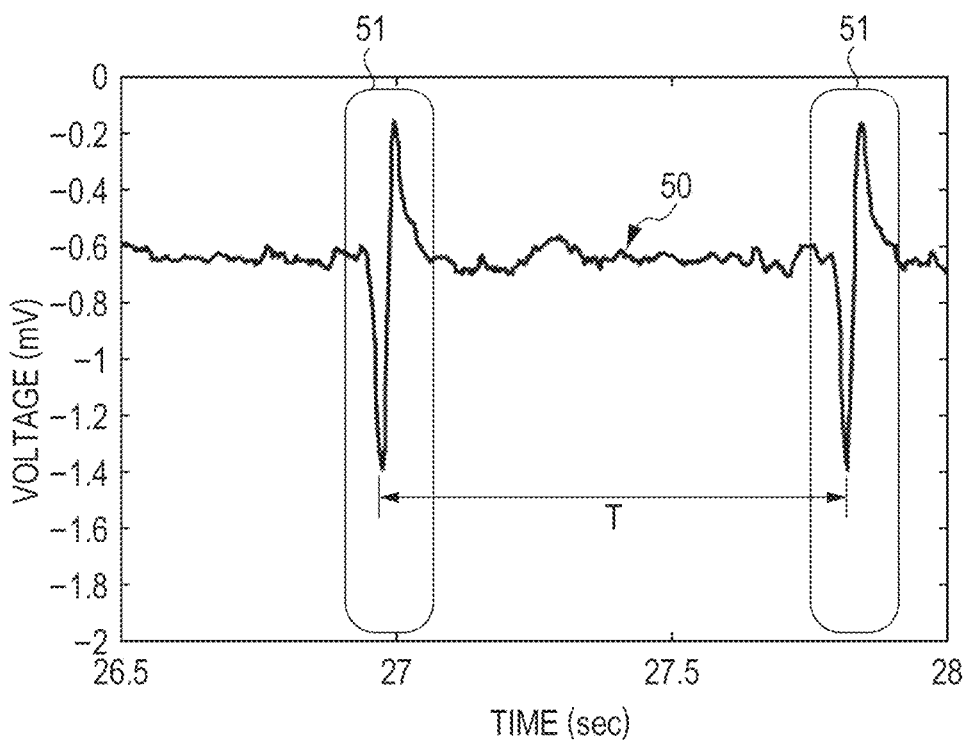
FIG. 2A is a graph depicting an example of ideal heartbeat waveform detected by a left- or right-hand electrode.

FIG. 2A is a graph illustrating an example of ideal heartbeat waveform detected from a left or right hand. In this graph, the vertical axis indicates voltage (mV), while the horizontal axis indicates time (seconds). The heartbeat signal 50 in this graph has a waveform representing an alternate-current component in an ideal heartbeat signal detected from the left or right hand of the driver. The heartbeat signal 50 includes impulse-like R waves 51 having a main frequency band of about 10-30 Hz. By detecting these R waves 51, the heartbeat of the driver may be measured. When the driver is drowsy, the R waves 51 tend to be detected at regular intervals T.

Figure 2B:
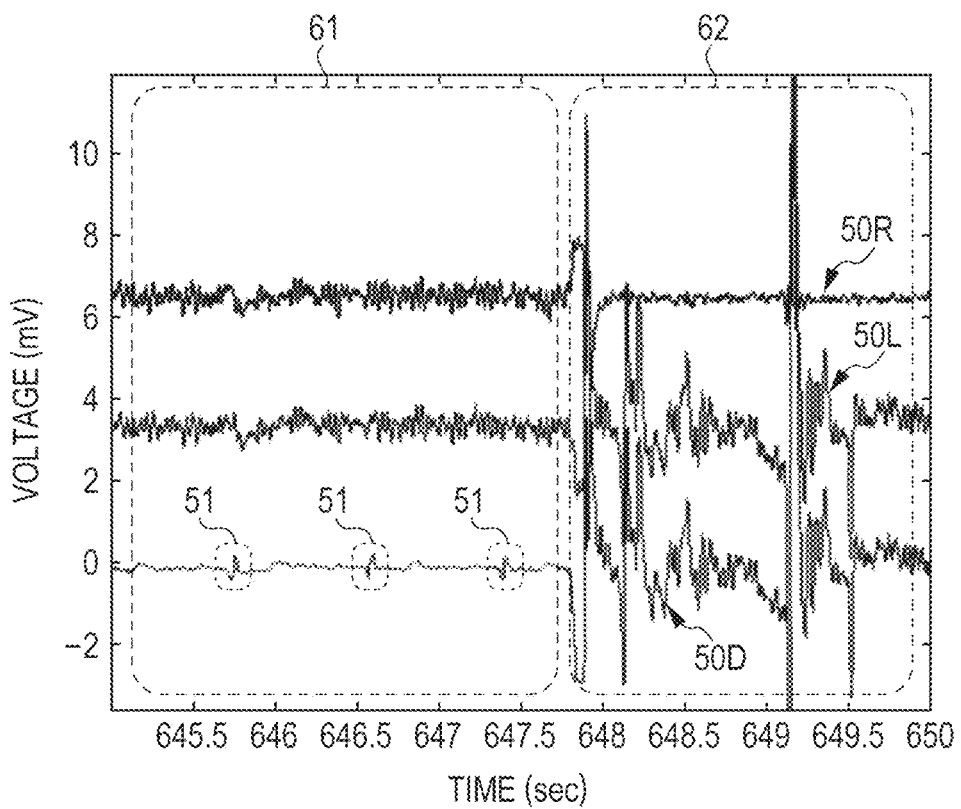
FIG. 2B is a graph depicting an example of actual heartbeat waveforms detected from left- and right-hand electrodes.

FIG. 2B is a graph representing an example of actual heartbeat waveforms detected from the left- and right-hand electrodes. In this graph, the vertical axis indicates voltage (mV), while the horizontal axis indicates time (seconds). The heartbeat signals 50L and 50R in this graph have waveforms representing the alternate-current components in the heartbeat signals detected by the left-hand electrode 10a (FIG. 1A) and right-hand electrode 10b (FIG. 1A). The section 61 in this graph is a section in which the driver is stably holding the electrode-equipped steering wheel 10 (FIG. 1A) with both hands; more specifically, the vehicle operated by the driver is moving straight ahead. The section 62 in this graph is a section in which the driver is not stably holding the electrode-equipped steering wheel with both hands; more specifically, the vehicle operated by the driver is turning right or left.

In section 61, in-phase noise signals (noise signals in phase with each other) are superimposed on the heartbeat signals 50L, 50R. It is difficult to detect R waves directly from the heartbeat signals 50L, 50R including such noise signals. In such a case, a differential heartbeat signal having the noise signals canceled out may be generated by amplifying the heartbeat signal 50L or 50R such that the amplitude values of the noise signals included in the heartbeat signals 50L and 50R become identical, and then calculating the difference between the heartbeat signals. An amplification factor for amplifying the heartbeat signal 50L or 50R may be calculated on the basis of the ratio between the amplitude values of the heartbeat signals 50L and 50R, for example.

The differential heartbeat signal 50D in this graph is generated by amplifying one of the heartbeat signals 50L and 50R and then calculating the difference between the heartbeat signals. As is apparent from the waveform of the differential signal 50D in section 61, the R waves 51 may be detected easily from the differential signal 50D. The amplitude value of the R waves 51 included in this differential signal 50D is about 0.2-1.8 mV, for example, depending on the driver. In this way, more accurate heartbeat measurement may be achieved by generating the differential signal 50D from the heartbeat signals 50L, 50R.

Since the problem discussed herein is to avoid drowsy driving, it is desirable that the heartbeat of a driver operating a vehicle is measured in real time. More specifically, it is desirable that the amplification factor to be applied to the heartbeat signal 50L or 50R in section 61 is calculated in advance from the heartbeat signals 50L, 50R in a section immediately preceding the section 61 and, upon detection of the heartbeat signals 50L, 50R in section 61, a differential signal 50D is generated by sequentially applying the amplification and difference calculation processes. This method of immediately generating a differential signal using a pre-calculated amplification factor will be referred to hereinafter as a real-time waveform generating method.

The noise signals included in the heartbeat signals 50L, 50R are not only the in-phase noise signals. As in the heartbeat signals 50L, 50R in section 62, out-of-phase noise signals (noise signals not in phase with each other) may be superimposed on the detected heartbeat signals depending on the status of the driver gripping the steering wheel. In such a case, it is desirable to exclude the section 62 from the target of heartbeat measurement, because, like the differential signal 50D in section 62, it is difficult to accurately measure the heartbeat even after the amplification and difference calculation processes are applied. When the real-time waveform generation method is employed, it is desirable, in the section immediately following the section 62, not to apply the amplification factor calculated on the basis of the heartbeat signals 50L, 50R in section 62. More specifically, it is desirable to apply the amplification factor calculated in a section preceding the section 62, such as section 61, in which the reliability of the detected heartbeat signals is high.

The present inventors studied a heartbeat signal processor capable of determining the status of the driver gripping the electrode-equipped steering wheel or the reliability of the detected heartbeat signals and setting an appropriate amplification factor to be applied to generate a differential signal. In the following, the general configuration of the heartbeat signal processor provided by the present inventors will be described first and then the functions of the components of the heartbeat signal processor will be described.

Figure 3:
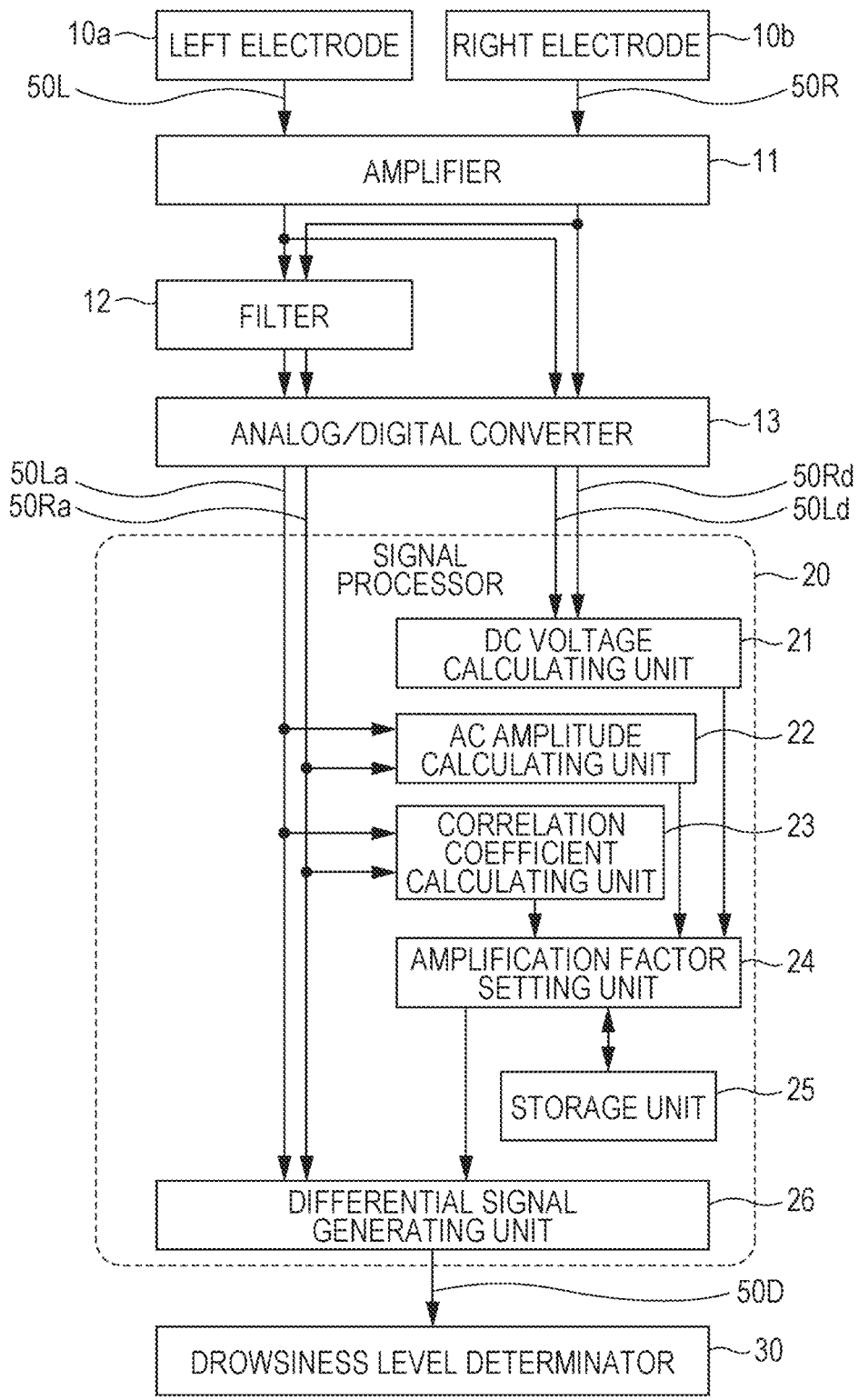
FIG. 3 is a diagram illustrating an exemplary configuration of a heartbeat signal processor provided by the present inventors.

FIG. 3 is a diagram illustrating an exemplary configuration of the heartbeat signal processor provided by the present inventors. This heartbeat signal processor includes electrodes 10a, 10b, an amplifier 11, a filter 12, an analog/digital converter (ADC) 13, and a signal processor 20.

When gripped by a driver with both hands, the electrodes 10a, 10b detect heartbeat signals 50L, 50R of this driver. The heartbeat signals 50L, 50R detected by the electrodes 10a, 10b are amplified by the amplifier 11. The heartbeat signals 50L, 50R amplified by the amplifier 11 are branched into two routes, respectively. The heartbeat signals 50L, 50R in one route pass through the bandpass filter 12 for attenuating, for example, the signals having frequency bands other than the main frequency band of 10-30 Hz of the R waves and enters the ADC 13. The heartbeat signals 50L, 50R in the other route enter directly the ADC 13 as they are.

The heartbeat signals 50L, 50R that have not passed through the filter 12 are signals including direct-current components (DC components) and will be referred to hereinafter as the DC signals 50Ld, 50Rd. The heartbeat signals 50L, 50R that have passed through the filter 12 are signals having the DC components cut off and mainly including alternate-current components (AC components) and will be referred to hereinafter as the AC signals 50La, 50Ra. The DC signals 50Ld, 50Rd and AC signals 50La, 50Ra are converted from analog to digital by the ADC 13 and then input to the signal processor 20. Preferably, the sampling frequency used for analog to digital conversion in the ADC 13 is not lower than 300 Hz.

The signal processor 20 includes a DC voltage calculating unit 21, AC amplitude calculating unit 22, correlation coefficient calculating unit 23, amplification factor setting unit 24, storage unit 25, and differential signal generating unit 26.

The DC signals 50Ld, 50Rd input to the signal processor 20 are input to the DC voltage calculating unit 21. The DC voltage calculating unit 21 calculates average DC voltage values of the DC signals 50Ld, 50Rd in a predetermined time period. The calculated average DC voltage values are communicated to the amplification factor setting unit 24.

The AC signals 50La, 50Ra input to the signal processor 20 are input to the AC amplitude calculating unit 22 and correlation coefficient calculating unit 23. The AC amplitude calculating unit 22 measures average AC amplitude values of the AC signals 50La, 50Ra in the predetermined time period. The calculated average AC amplitude values are communicated to the amplification factor setting unit 24. The correlation coefficient calculating unit 23 calculates a correlation coefficient between the AC signals 50La and 50Ra in the predetermined time period. The calculated correlation coefficient is communicated to the amplification factor setting unit 24.

On the basis of the average DC voltage values, average AC amplitude values, and correlation coefficient communicated, respectively, from the DC voltage calculating unit 21, the AC amplitude calculating unit 22, and the correlation coefficient calculating unit 23, the amplification factor setting unit 24 determines the status of the driver gripping the steering wheel or the reliability of the detected heartbeat signals, especially of the AC signals 50La, 50Ra. Depending on this determination result, the amplification factor setting unit 24 sets an amplification factor for amplifying the AC signal 50La or 50Ra. The amplification factor setting unit 24 may store in the storage unit 25 the calculated data communicated from the calculating units as well as the amplification factor calculated on the basis of these data.

The AC signals 50La, 50Ra input to the signal processor 20 are further input to the differential signal generating unit 26. On the basis of the amplification factor set by the amplification factor setting unit 24, the differential signal generating unit 26 amplifies one of the AC signals 50La and 50Ra, and then calculates a difference between the amplified AC signal and the other AC signal, generating a differential signal 50D. The differential signal generating unit 26 outputs the generated differential signal 50D to a device in a later stage, such as a drowsiness level determinator 30 for determining the drowsiness level of the driver on the basis of the R waves included in the differential signal 50D, for example.

With such a configuration, it is possible to obtain a heartbeat signal processor capable of determining the status of the driver gripping the electrode-equipped steering wheel or the reliability of the detected heartbeat signals. Next, specific processes performed by the DC voltage calculating unit 21, AC amplitude calculating unit 22, correlation coefficient calculating unit 23, and amplification factor setting unit 24 will be described with reference to the waveforms of the DC signals 50Ld, 50Rd and AC signals 50La, 50Ra.

Figure 4A:
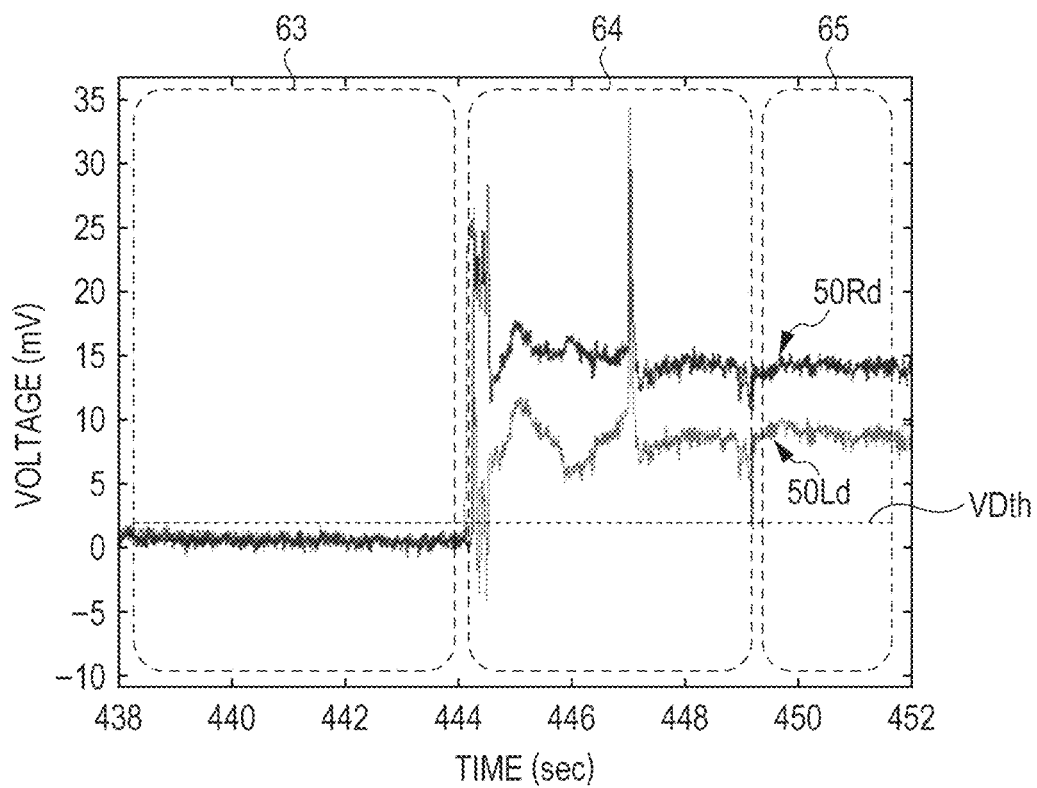
FIG. 4A is a graph depicting waveforms of DC signals in heartbeat signals.
Figure 4B:
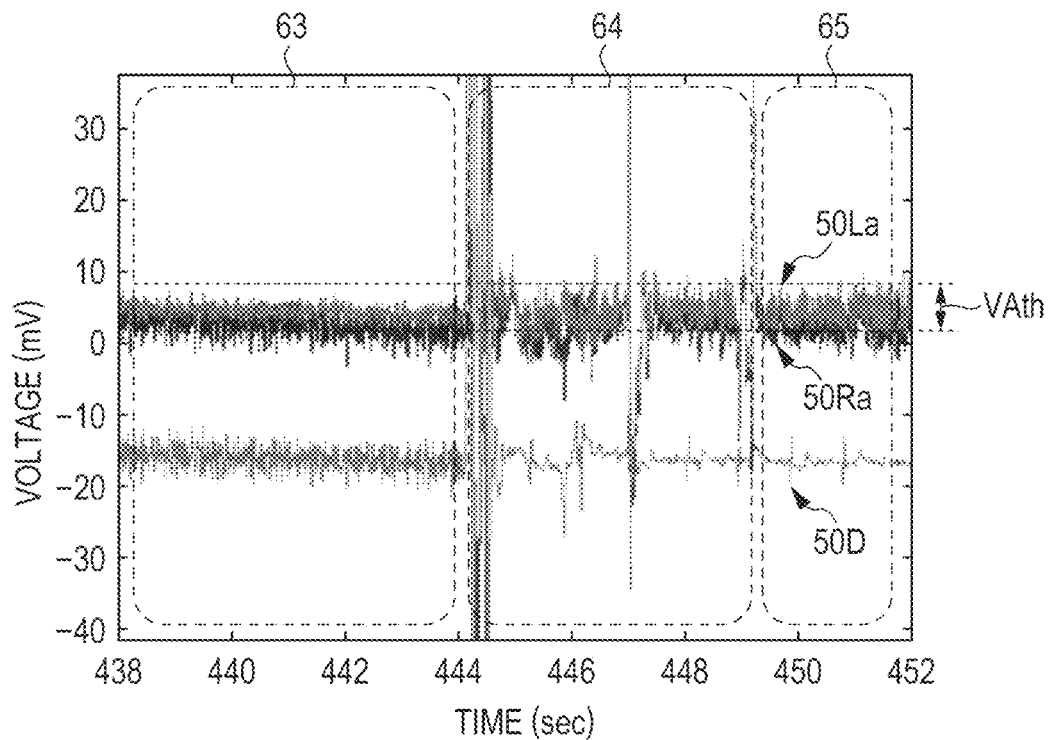
FIG. 4B is a graph depicting waveforms of AC signals in the heartbeat signals illustrated in FIG. 4A.

FIGS. 4A and 4B are graphs representing the waveforms of the DC signals 50Ld, 50Rd and AC signals 50La, 50Ra. In these graphs, the vertical axis indicates voltage (mV), while the horizontal axis indicates time (seconds). The section 63 in these graphs is a section in which the driver is not holding the electrode-equipped steering wheel with both hands; more specifically, the vehicle operated by the driver is waiting at a traffic light, for example. The section 64 in these graphs is a section in which the driver is not stably holding the electrode-equipped steering wheel with both hands; more specifically, the vehicle operated by the driver is turning right or left. The section 65 in these graphs is a section in which the driver is stably holding the electrode-equipped steering wheel; more specifically, the vehicle operated by the driver is moving straight ahead.

As known from the graph in FIG. 4A, in section 63 in which the driver is not holding the electrode-equipped steering wheel with both hands, voltages of the direct-current components in the DC signals 50Ld, 50Rd are not detected almost at all. In sections 64, 65 in which the driver is holding the electrode-equipped steering wheel with both hands, voltages of at least about 5 mV are detected from the direct-current components in the DC signals 50Ld, 50Rd. In section 64 in which the driver is not stably holding the electrode-equipped steering wheel, large out-of-phase noise signals are superimposed on the DC signals 50Ld, 50Rd. From the graph illustrated in FIG. 4A, it may be seen that the status of the driver holding or not holding the steering wheel may be determined on the basis of the voltage values of the direct-current components in the heartbeat signals.

The DC voltage calculating unit 21 calculates average DC voltage values VLd, VRd from the detected DC signals 50Ld, 50Rd in each of the predetermined time periods (e.g., 5 seconds each). The average DC voltage values VLd, VRd of the DC signals 50Ld, 50Rd are root mean square (RMS) voltage values or effective voltage values in a predetermined time period, for example.

The amplification factor setting unit 24 compares the average DC voltage values VLd, VRd calculated by a DC voltage calculating unit 21 with a preset threshold value VDth (e.g., 1 mV). When the average DC voltage value VLd or VRd is lower than the threshold value VDth, it is determined that the driver is not holding the steering wheel with both hands. When the average DC voltage values VLd and VRd are equal to or higher than the threshold value VDth, it is determined that the driver is holding the steering wheel with both hands.

As known be seen from the graph illustrated in FIG. 4B, in section 64 in which the driver is not stably holding the electrode-equipped steering wheel, the amplitudes of the AC signals 50La, 50Ra are relatively large due to superimposed out-of-phase noise signals. On the other hand, in section 65 in which the driver is stably holding the electrode-equipped steering wheel with both hands, the amplitudes of the AC signals 50La, 50Ra are relatively small.

The correlationship between the AC signals 50La and 50Ra was actually examined on the basis of the graph illustrated in FIG. 4B and it was confirmed that there was a strong correlationship between the AC signals 50La and 50Ra in section 65. It was also confirmed that this correlationship was relatively low in section 64 due to superimposed out-of-phase noise signals.

As known from the graph illustrated in FIG. 4B and the examination of the correlationship, the stability of the status of the driver gripping the steering wheel may be determined on the basis of the amplitude values of the alternate-current components in the heartbeat signals and the correlationship therebetween.

The AC amplitude calculating unit 22 calculates average AC amplitude values VLa, VRa from the detected AC signals 50La, 50Ra in each predetermined time period. The correlation coefficient calculating unit 23 calculates a correlation coefficient C between the AC signals 50La and 50Ra in each predetermined time period.

The amplification factor setting unit 24 compares the average AC amplitude values VLa, VRa calculated by the AC amplitude calculating unit 22 with a preset threshold value VAth (e.g., 5 mV). The amplification factor setting unit 24 also compares the correlation coefficient C calculated by the correlation coefficient calculating unit 23 with a preset threshold value Cth. When the average AC amplitude value VLa or VRa is higher than the threshold value VAth and the correlation coefficient C is lower than the threshold value Cth, the amplification factor setting unit 24 determines that the driver is not stably gripping the electrode-equipped steering wheel with both hands. When the average AC amplitude values VLa and VRa are not higher than the threshold value VAth or the correlation coefficient C is not lower than the threshold value Cth, the amplification factor setting unit 24 determines that the driver is stably gripping the electrode-equipped steering wheel with both hands.

Figure 5:
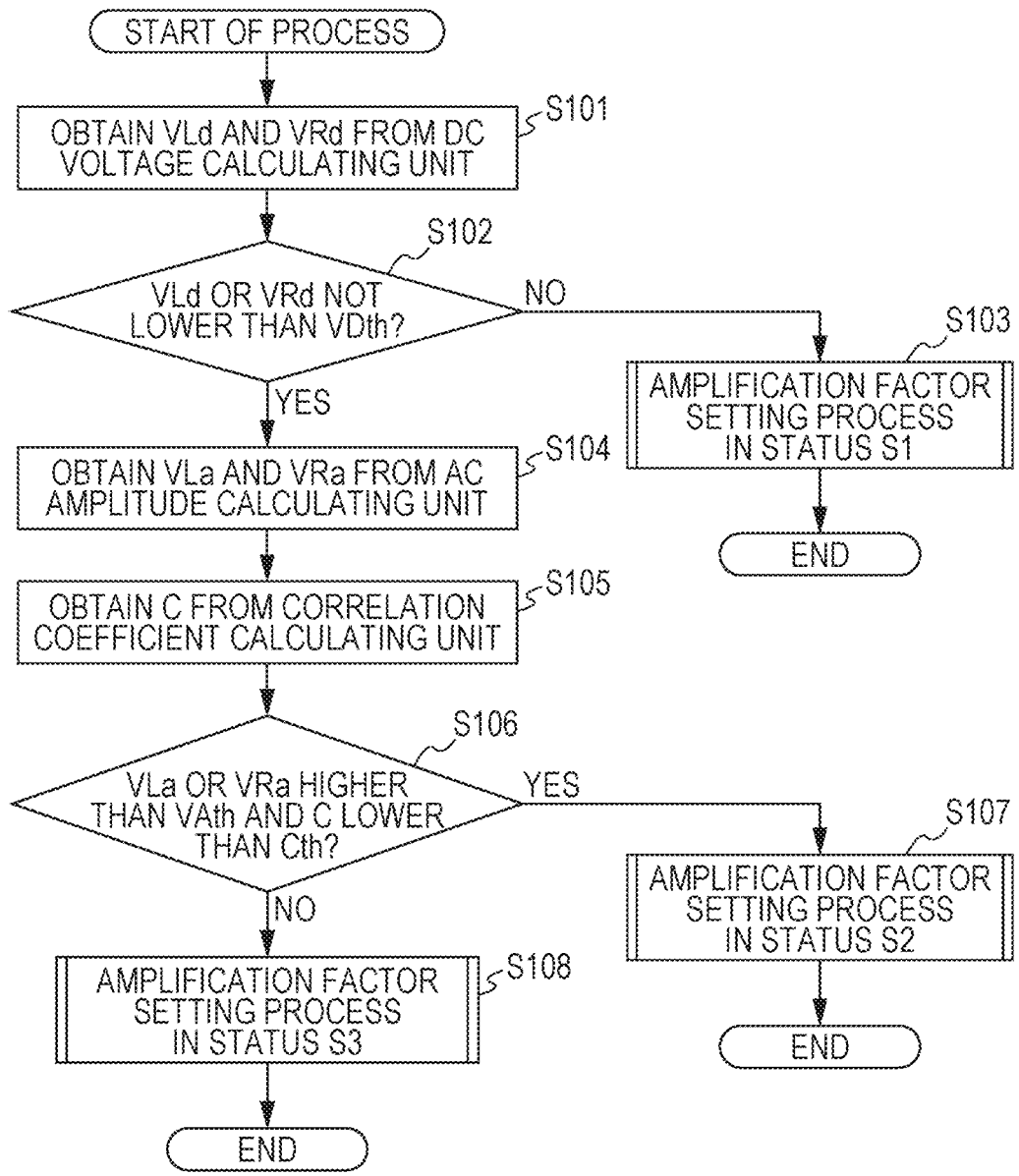
FIG. 5 is a flowchart illustrating an exemplary process in which an amplification factor setting unit determines the status of the driver gripping the steering wheel or the reliability of the detected heartbeat signals, on the basis of average DC voltage values, average AC amplitude values, and a correlation coefficient.

FIG. 5 is a flowchart illustrating an exemplary process in which the amplification factor setting unit 24 determines the status of the driver gripping the steering wheel on the basis of the average DC voltage values VLd, VRd, average AC amplitude values VLa, VRa, and the correlation coefficient.

First, the amplification factor setting unit 24 obtains average DC voltage values VLd, VRd in a predetermined time period from the DC voltage calculating unit 21 (S101). The amplification factor setting unit 24 then compares the average DC voltage values VLd, VRd with a preset threshold value VDth (S102).

In step S102, if the average DC voltage value VLd or VRd is lower than the threshold value VDth, the amplification factor setting unit 24 determines that the driver is in a status not holding the electrode-equipped steering wheel with both hands (status S1). If the average DC voltage values VLd and VRd are not lower than the threshold value VDth, the amplification factor setting unit 24 proceeds to the next step S104.

Then, the amplification factor setting unit 24 obtains average AC amplitude values VLa, VRa in the predetermined time period from the AC amplitude calculating unit 22 (S104). The amplification factor setting unit 24 also obtains a correlation coefficient C in the predetermined time period from the correlation coefficient calculating unit 23 (S105). The amplification factor setting unit 24 compares the average AC amplitude values VLa, VRa with a preset threshold value VAth and then compares the correlation coefficient C with a preset threshold value Cth (S106).

In step S106, if the average AC amplitude value VLa or VRa is higher than the threshold value VAth and the correlation coefficient C is lower than the threshold value Cth, the amplification factor setting unit 24 determines that the driver is in a status not stably gripping the electrode-equipped steering wheel with both hands (status S2) (S107). If the average AC amplitude values VLa and VRa are not higher than the threshold value VAth or the correlation coefficient C is not lower than the threshold value Cth, the amplification factor setting unit 24 determines that the driver is in a status stably gripping the electrode-equipped steering wheel with both hands (status S3) (S108).

Here, the time period in which the DC voltage calculating unit, AC amplitude calculating unit, and correlation coefficient calculating unit calculate average DC voltage values, average AC amplitude values, and correlation coefficient, respectively, will be assumed to be a first time period. The time period immediately following the first time period will be assumed to be a second time period and the time period immediately preceding the first time period will be assumed to be a third time period. Preferably, each of the first to third time periods is longer than a time period converted from the main frequency band 10-30 Hz of the R waves. More specifically, each of the first to third time periods is preferably longer than 0.1 seconds, i.e., the value converted from the main frequency band of the R waves. Next, processes to be performed when the amplification factor setting unit 24 determines that the driver is in the statuses S1-S3 will be described.

When the status of the driver gripping the steering wheel is determined to be status S3, the amplification factor setting unit 24 determines that the reliability of the detected heartbeat signals is high. The amplification factor setting unit 24 then calculates a first amplification factor from the amplitude ratio between the AC signals 50La, 50Ra in the first time period, i.e., from the ratio between the average AC amplitude values VLa, VRa in the first time period, for example. The amplification factor setting unit 24 also sets a first amplification factor as the amplification factor to be applied by the differential signal generating unit 26 to the AC signal 50La or 50Ra in the second time period. The differential signal generating unit 26, therefore, instantaneously generates a differential signal 50D in the second time period using the first amplification factor.

When the status of the driver gripping the steering wheel is determined to be status S1 or S2, the amplification factor setting unit 24 determines that the reliability of the detected heartbeat signals is low. The amplification factor setting unit 24 then sets a second amplification factor calculated from the amplitude ratio between the AC signals 50La, 50Ra in the third time period as the amplification factor to be applied by the differential signal generating unit 26 to the AC signal 50La or 50Ra in the second time period. It is assumed here that, in the third time period, the status of the driver gripping the steering wheel was determined to be status S3 and the reliability of the detected heartbeat signals was determined to be high. The differential signal generating unit 26, therefore, instantaneously generates a differential signal 50D in the second time period using the second amplification factor. Alternatively, the amplification factor setting unit 24 may store in the storage unit 25 the second amplification factor calculated in the third time period and may read in the first time period the second amplification factor from the storage unit 25 and set the second amplification factor in the differential signal generating unit 26.

By using the heartbeat signal processor described above, the status of the driver gripping the electrode-equipped steering wheel or the reliability of the detected heartbeat signals may be determined and an amplification factor to be applied to generate a differential signal may be appropriately set. Additional conditions may be included in the criteria to be used by the amplification factor setting unit 24 to determine the reliability of heartbeat signals. For example, when the status of the driver gripping the steering wheel is determined to be status S2 (i.e., the driver is not stably gripping the electrode-equipped steering wheel with both hands), frequency components included in the heartbeat signals may also be evaluated to determine the reliability of the detected heartbeat signals. This is because, even if out-of-phase noise signals are superimposed on the heartbeat signals, as long as the frequencies of the out-of-phase noise signals are lower than the main frequency band of the R waves, the out-of-phase noise signals exert little influence on the calculated amplification factor.

Figure 6A:
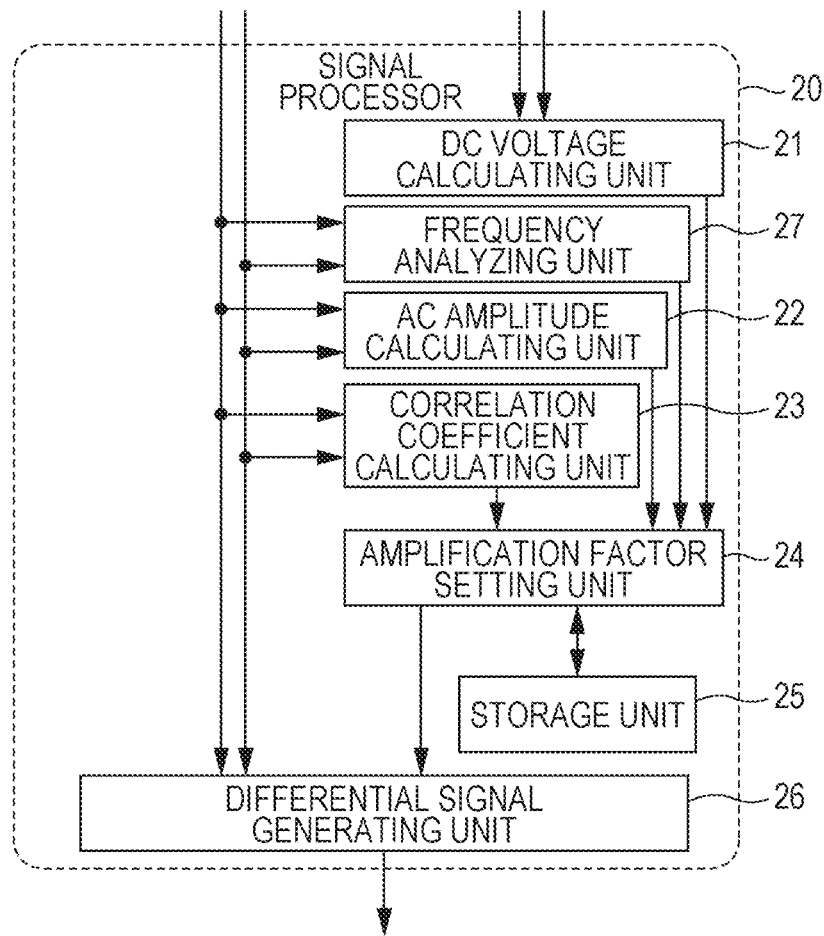
FIG. 6A is a diagram illustrating a part of another exemplary configuration of a heartbeat signal processor provided by the present inventors.
Figure 6B:
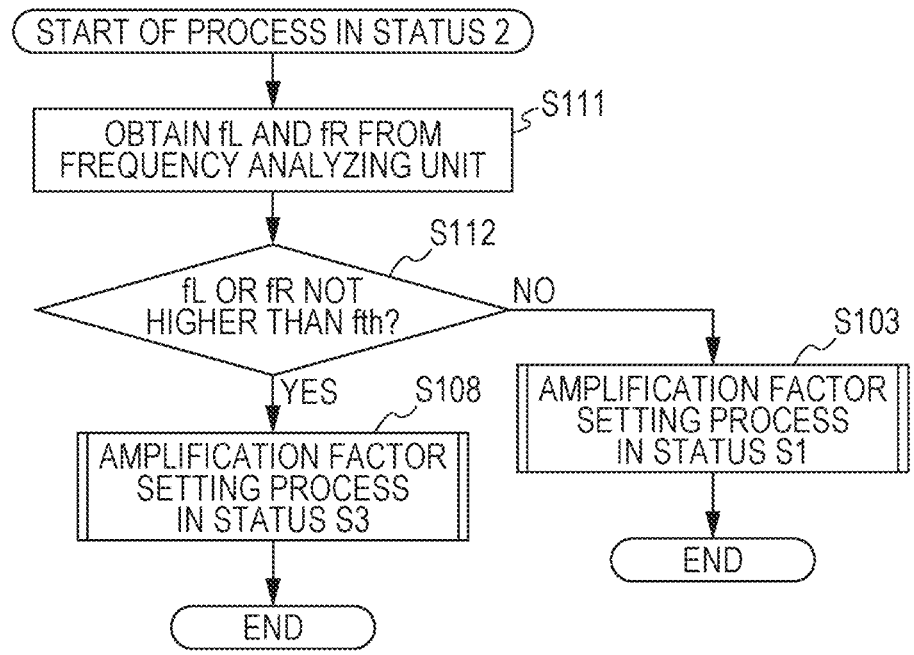
FIG. 6B is a flowchart illustrating a part of another exemplary process for determining the reliability of a heartbeat signal.

FIG. 6A is a diagram illustrating a part of another exemplary configuration of a heartbeat signal processor provided by the present inventors, while FIG. 6B is a flowchart illustrating a part of another exemplary process in which the reliability of heartbeat signals is determined.

As illustrated in FIG. 6A, the signal processor 20 may include a frequency analyzing unit 27. The frequency analyzing unit 27 analyzes frequency components fL, fR included in the AC signals 50La, 50Ra in a predetermined time period and communicates the analysis result to the amplification factor setting unit 24. The frequency analyzing unit 27 may analyze the frequency components included in the AC signals 50La, 50Ra through Fourier transformation of the AC signals 50La, 50Ra, for example.

When the status of the driver gripping the steering wheel is determined to be status S2 in the process described above, the amplification factor setting unit 24, as illustrated in FIG. 6B, further obtains frequency components fL, fR from the frequency analyzing unit 27 (S111), and compares the frequency components fL, fR with a preset threshold value fth (S112). Preferably, the threshold value fth is not higher than 10 Hz, for example, which is the lower limit of the main frequency band of the R waves. When the frequency component fL or fR is not higher than the threshold value fth, the amplification factor setting unit 24 determines that the reliability of the detected heartbeat signals is high and calculates the first amplification factor and sets the calculated first amplification factor in the differential signal generating unit 26, as in the amplification factor setting process for status S3. When the frequency component fL or fR is higher than the threshold value fth, the amplification factor setting unit 24 determines that the reliability of the detected heartbeat signals is low and sets in the differential signal generating unit 26 the second amplification factor stored in the storage unit 25, as in the amplification factor setting process for status S1.

By additionally evaluating the frequency components in the heartbeat signals when determining the reliability of the detected heartbeat signals, a more appropriate amplification factor may be set to generate a differential signal. The present inventors carried out an experiment in which the heartbeat of a driver actually driving a vehicle was measured using the heartbeat signal processor described above.

Figure 7:
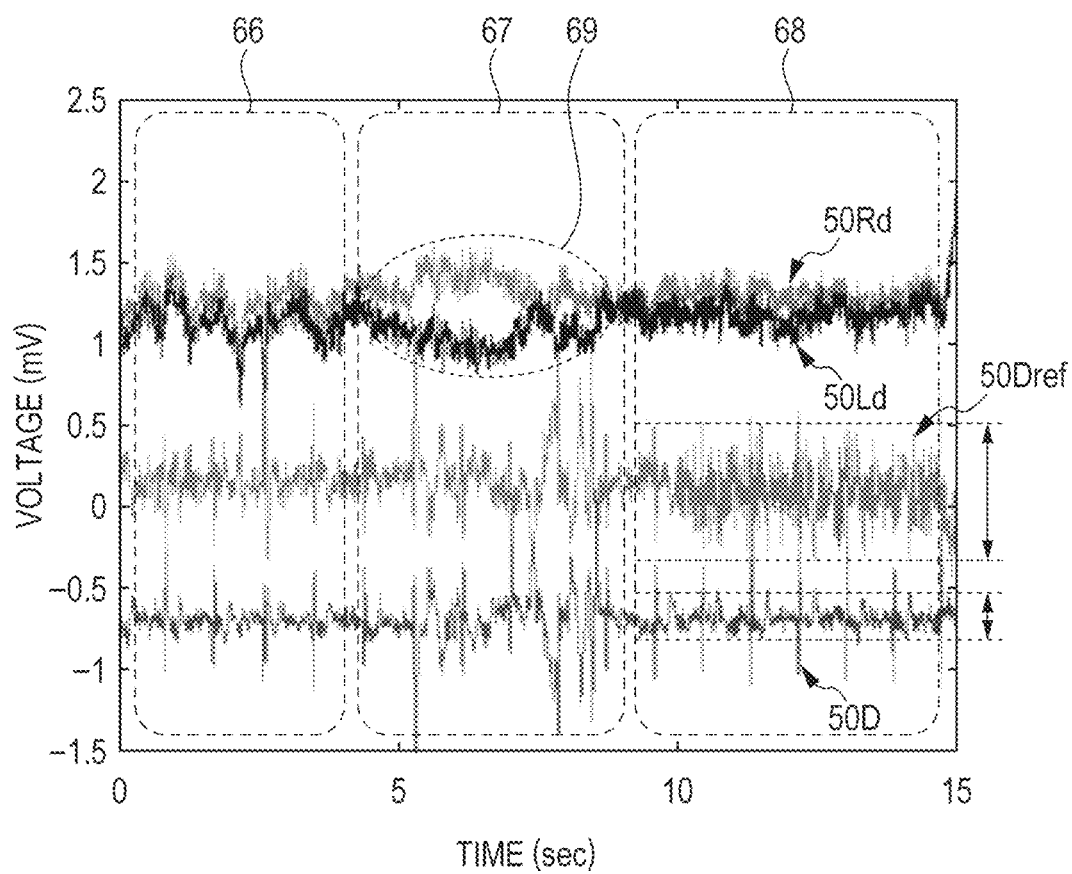
FIG. 7 is a graph representing the waveforms of DC signals and a differential heartbeat signal obtained by measuring the heartbeat of a driver actually driving a vehicle using the heartbeat signal processor provided by the present inventors.

FIG. 7 is a graph representing the waveforms of the DC signals and differential heartbeat signal obtained in this experiment. In this graph, the vertical axis indicates voltage (mV), while the horizontal axis indicates time (seconds). The sections 66 and 68 in this graph are sections in which the driver is stably gripping the electrode-equipped steering wheel; more specifically, the vehicle operated by the driver is moving straight ahead. The section 67 in this graph is a section in which the driver is not stably gripping the electrode-equipped steering wheel with both hands; more specifically, the vehicle operated by the driver is changing lanes.

As described above, the differential signal 50D in this graph is a waveform of the differential signal on which an amplification factor to be applied to a heartbeat signal (AC signal) is set on the basis of the average DC voltage values, average AC amplitude values, correlation coefficient, and frequency components of the heartbeat signals in a predetermined time period. The reference differential signal 50Dref in this graph is a waveform of the differential signal on which the amplification factor to be applied to the heartbeat signal (AC signal) is set solely on the basis of the amplitude values of the alternate-current components in the heartbeat signals in the predetermined time period.

It may be seen from this graph that out-of-phase noises 69 gradually changing in voltage are superimposed on the DC signals 50Ld, 50Rd in the section 67. It may also be seen that the amplitude values of the alternate-current components in these out-of-phase noises 69 are not so high. It may also be seen from the waveforms of the differential signal 50D and reference differential signal 50Dref in section 68 that the noise signal (mainly, in-phase noise signal) is more reduced in the differential signal 50D than in the reference differential signal 50Dref.

When generating a differential signal 50D in section 68, the amplification factor setting unit 24 detects the out-of-phase noise signals 69 in section 67 and determines that the reliability of the heartbeat signals in this section is low, and applies the amplification factor calculated on the basis of the heartbeat signals (AC signals) in section 66 to a heartbeat signal in section 68. Since the amplification factor calculated on the basis of the heartbeat signals of the driver stably gripping the steering wheel is applied to a heartbeat signal in section 68, noise components are sufficiently reduced in the differential signal 50D in section 68.

In contrast, when generating a reference differential signal 50Dref in section 68, the amplification factor setting unit 24 fails to detect out-of-phase noises 69 due to small amplitude values of the alternate-current components in the out-of-phase noises 69 and applies an amplification factor calculated on the basis of the heartbeat signals in section 67 to a heartbeat signal in section 68. Since the amplification factor calculated on the basis of the heartbeat signals of the driver unstably gripping the steering wheel is applied to the heartbeat signal in section 68, noise components are not sufficiently reduced in the reference differential signal 50Dref in section 68.

The results of this experiment confirmed the usefulness of the heartbeat signal processor and heartbeat signal processing method provided by the present inventors. By using the heartbeat signal processor or heartbeat signal processing method provided by the present inventors, more accurate heartbeat measurement will be enabled.

The present invention has been described above with reference to the preferred embodiments, but the present invention is not limited to these embodiments. For example, the components of the heartbeat signal processor may be implemented as a single device, instead of separate components, having the functions of the individual components. It will be apparent to those skilled in the art that various variations, modifications, combinations, etc., are possible.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A heartbeat signal processor comprising:
   a first electrode configured to be gripped with one hand to detect a first heartbeat signal, the first heartbeat signal being a potential difference signal with respect to a ground;
   a second electrode configured to be gripped with another hand to detect a second heartbeat signal, the second heartbeat signal being another potential difference signal with respect to the ground;
   a DC voltage calculating unit configured to calculate first and second average DC voltage values as voltage values of direct-current components in the first and second heartbeat signals;
   an AC amplitude calculating unit configured to calculate first and second average AC amplitude values as amplitude values of alternate-current components in the first and second heartbeat signals;
   a correlation coefficient calculating unit configured to calculate a correlation coefficient between the alternate-current component in the first heartbeat signal and the alternate-current component in the second heartbeat signal;
   an amplification factor setting unit configured to set an amplification factor for amplifying the first or second heartbeat signal on the basis of the first and second average DC voltage values, the first and second average AC amplitude values, and the correlation coefficient; and a signal generating unit configured to generate a differential heartbeat signal by amplifying the first or second heartbeat signal on the basis of the amplification factor set by the amplification factor setting unit and calculating a difference between the first and second heartbeat signals.

2. The heartbeat signal processor according to claim 1, wherein, in a second time period, the second time period being a time period after a first time period, the amplification factor setting unit determines a reliability of the first and second heartbeat signals in the first time period on the basis of the first and second average DC voltage values, the first and second average AC amplitude values, and the correlation coefficient in the first time period, and sets an amplification factor to be applied to the first or second heartbeat signal in the second time period on the basis of the reliability determination.

3. The heartbeat signal processor according to claim 2, further comprising:
a frequency analyzing unit configured to analyze first and second frequency components included in the first and second heartbeat signals;
wherein the amplification factor setting unit further determines the reliability of the first and second heartbeat signals in the first time period on the basis of the first and second frequency components in the first time period.

4. The heartbeat signal processor according to claim 2, wherein the amplification factor setting unit sets a first amplification factor calculated on the basis of the first and second heartbeat signals in the first time period as an amplification factor to be applied to the first or second heartbeat signal in the second time period when the reliability of the first and second heartbeat signals in the first time period is determined to be high.

5. The heartbeat signal processor according to claim 2, wherein the amplification factor setting unit sets a second amplification factor calculated on the basis of the first and second heartbeat signals in a third time period, the third time period being a time period before the first time period, as an amplification factor to be applied to the first or second heartbeat signal in the second time period when the reliability of the first and second heartbeat signals in the first time period is determined to be low.

6. The heartbeat signal processor according to claim 3, wherein the amplification factor setting unit sets a first amplification factor calculated on the basis of the first and second heartbeat signals in the first time period as an amplification factor to be applied to the first or second heartbeat signal in the second time period when the reliability of the first and second heartbeat signals in the first time period is determined to be high.

7. The heartbeat signal processor according to claim 3, wherein the amplification factor setting unit sets a second amplification factor calculated on the basis of the first and second heartbeat signals in a third time period, the third time period being a time period before the first time period, as an amplification factor to be applied to the first or second heartbeat signal in the second time period when the reliability of the first and second heartbeat signals in the first time period is determined to be low.

* * * * *